US011413061B2

(12) United States Patent
Aikawa et al.

(10) Patent No.: US 11,413,061 B2
(45) Date of Patent: Aug. 16, 2022

(54) MEDICAL TOOL FOR ENDOSCOPE

(71) Applicant: OLYMPUS CORPORATION, Hachioji (JP)

(72) Inventors: Yoshie Aikawa, Tokyo (JP); Takayasu Mikkaichi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1244 days.

(21) Appl. No.: 15/876,852

(22) Filed: Jan. 22, 2018

(65) Prior Publication Data
US 2018/0140320 A1    May 24, 2018

Related U.S. Application Data

(63) Continuation of application No. PCT/JP2016/061366, filed on Apr. 7, 2016.

(30) Foreign Application Priority Data

Jul. 24, 2015    (JP) .............................. JP2015-146999

(51) Int. Cl.
*A61B 17/3205*    (2006.01)
*A61B 1/00*    (2006.01)
(Continued)

(52) U.S. Cl.
CPC ...... *A61B 17/32056* (2013.01); *A61B 1/0008* (2013.01); *A61B 1/00087* (2013.01);
(Continued)

(58) Field of Classification Search
CPC .............. A61B 17/32056; A61B 1/008; A61B 2017/00269
See application file for complete search history.

(56) References Cited

U.S. PATENT DOCUMENTS

2004/0158127 A1    8/2004    Okada
2004/0210111 A1    10/2004    Okada
(Continued)

FOREIGN PATENT DOCUMENTS

JP    2004-230053 A    8/2004
JP    2004-230054 A    8/2004
(Continued)

OTHER PUBLICATIONS

Suzuki, JP 2010 022697 A (CAP, published Feb. 4, 2010, English Translation of Description) (Year: 2010).*
(Continued)

*Primary Examiner* — Ronald Hupczey, Jr.
(74) *Attorney, Agent, or Firm* — Oliff PLC

(57) ABSTRACT

A medical device includes a snare wire advanceable and retractable inserted through a channel in an insertion portion that is inserted through an endoscope; a substantially tubular cap member including a first portion and a second portion connected to a distal end of the insertion portion, the cap member having an annular distal end surface, the first portion being attachable to the distal end of the insertion portion in phase with the channel, and the cap member having an internal space formed by the first portion and the second portion; and a guide member being linearly extended along an internal surface of the distal end side of the cap member at a side of the second portion, the guide member being configured to guide the snare wire to form a loop and to restrict a retraction of the snare wire toward the side of the insertion portion.

15 Claims, 11 Drawing Sheets

(51) Int. Cl.
 *A61B 1/018* (2006.01)
 *A61B 18/14* (2006.01)
 *A61B 18/00* (2006.01)
 *A61B 17/30* (2006.01)
 *A61B 17/32* (2006.01)
 *A61B 17/29* (2006.01)
 *A61B 17/34* (2006.01)
 *A61B 17/00* (2006.01)

(52) U.S. Cl.
 CPC ...... *A61B 1/00098* (2013.01); *A61B 1/00101* (2013.01); *A61B 1/018* (2013.01); *A61B 18/1492* (2013.01); *A61B 17/29* (2013.01); *A61B 17/3478* (2013.01); *A61B 2017/00269* (2013.01); *A61B 2017/00296* (2013.01); *A61B 2017/306* (2013.01); *A61B 2017/320064* (2013.01); *A61B 2018/00172* (2013.01); *A61B 2018/00291* (2013.01); *A61B 2018/00595* (2013.01); *A61B 2018/00601* (2013.01); *A61B 2018/141* (2013.01)

(56) References Cited

U.S. PATENT DOCUMENTS

2005/0033115 A1  2/2005  Okada
2014/0194684 A1* 7/2014  Raymondos ...... A61M 16/0488
                                                600/109

FOREIGN PATENT DOCUMENTS

| JP | 2004-230139 A | 8/2004 |
| JP | 2005-058343 A | 3/2005 |
| JP | 2010-022697 A | 2/2010 |
| JP | 2010-042084 A | 2/2010 |

OTHER PUBLICATIONS

Suzuki, JP 2010 022697 A (CAP, published Feb. 4, 2010, English Translation of Diagrams) (Year: 2010).*

Jul. 5, 2016 International Search Report issued in International Patent Application No. PCT/JP2016/061366.

* cited by examiner

MEDICAL TOOL FOR ENDOSCOPE

BACKGROUND OF THE INVENTION

Field of the Invention

The present invention relates to a medical device.

This application is a continuation application based on a PCT International Application No. PCT/JP2016/061366, filed on Apr. 7, 2016, whose priority is claimed on Japanese Patent Application No. 2015-146999, filed on Jul. 24, 2015. The contents of both the POT International Application and the Japanese Patent Application are incorporated herein by reference.

Description of Related Art

Recently, Endoscopic Mucosal Resection (EMR) receives a lot of attention as a therapeutic approach for treating an early-stage cancer. As an aspect of the EMR, a procedure (EMR using a cap: EMRC) using a medical device which is configured by attaching a transparent cap at a distal end of an insertion portion of an endoscope is known (For example, referring to Japanese Unexamined Patent Application, First Publication No. 2004-230053).

According to the medical device disclosed in Japanese Unexamined Patent Application, First Publication No 2004-230053, a claw portion projecting inwardly is formed on an internal circumference surface of a distal end portion of the cap. When an operator resects the mucous membrane, the operator projects a snare wire of a high-frequency snare to the inside of the cap and the operator hooks the snare wire on the claw portion to form a pre-loop. The operator then suctions the mucous membrane into the cap, uses the loop-shaped snare wire to bind the mucous membrane, and energizes the high-frequency snare for resecting a base portion of the mucous membrane.

SUMMARY OF THE INVENTION

According to a first aspect of the present invention, a medical device includes a snare wire which is advanceable and retractable inserted through a channel formed inside an insertion portion, the insertion portion being inserted through an endoscope; a substantially tubular cap member which includes a first portion and a second portion, the first portion and the second portion being connected to a distal end of the insertion portion, the cap member having an annular distal end surface at the distal end thereof, the first portion being attachable to the distal end of the insertion portion in phase with the channel, and the cap member having an internal space formed by the first portion and the second portion; and a guide member which is configured to be linearly extended along an internal surface of the distal end side of the cap member at a side of the second portion, the guide member being configured to guide the snare wire to form a loop along the internal surface and to restrict a retraction of the snare wire toward the side of the insertion portion, wherein, in a lateral view of the cap member, the guide member is configured such that an angle formed between an extending direction of the guide member and an axis line of the cap member is different from an angle formed between the annular distal end surface and the axis line of the cap member.

According to a second aspect of the present invention, in the medical device according to the first aspect, two end portions of the guide member may extend toward the first portion respectively, and in the lateral view of the cap member, the guide member and an axis line of the cap member may be intersected with each other to form an acute angle at a proximal end side of the cap member.

According to a third aspect of the present invention, in the medical device according to the second aspect, a length from a distal end surface to a proximal end surface of the cap member at the side of the first portion may be shorter than a length from the distal end surface to the proximal end surface of the cap member at the side of the second portion.

According to a fourth aspect of the present invention, in the medical device according to the first aspect, the guide member may include a parallel portion which is parallel to the distal end surface of the cap member at least at the side of the second portion.

According to a fifth aspect of the present invention, in the medical device according to the first aspect, a region in which the guide member is disposed may be smaller than a half of an internal circumference surface of the cap member.

According to a sixth aspect of the present invention, the medical device according to any one of the first aspect to the fourth aspect may further include a restriction member which is disposed in the internal space at a side of the first portion of the cap member in order to define a projecting direction of the snare wire projecting from the channel and to restrict a movement of the snare wire toward a horizontal direction intersecting with a longitudinal axis of the channel.

According to a seventh aspect of the present invention, in the medical device according to the sixth aspect, the restriction member may be a tube body through which the snare wire is able to be inserted.

According to an eighth aspect of the present invention, in the medical device according to the seventh aspect, a center axis of the tube body may be inclined with the longitudinal axis of the channel.

According to a ninth aspect of the present invention, in the medical device according to the seventh aspect, an internal diameter of a distal end of the tube body may be smaller than an internal diameter of the channel.

According to a tenth aspect of the present invention, in the medical device according to the sixth aspect, the restriction member may be fixed to an internal surface of the cap member, the internal surface and a center axis of the internal space being on opposite sides with respect to the longitudinal axis of the channel.

According to an eleventh aspect of the present invention, in the medical device according to the sixth aspect, the restriction member may be disposed in the internal space of the cap member in a manner that a proximal end of the restriction member is spaced away from a distal end of the insertion portion.

According to a twelfth aspect of the present invention, in the medical device according to the sixth aspect, a communication hole may be formed at a proximal end side of the restriction member for communicating with the internal space.

According to a thirteenth aspect of the present invention, in the medical device according to the sixth aspect, a notch may be formed at the side of the second portion at the proximal end side of the restriction member.

According to a fourteenth aspect of the present invention, in the medical device according to the sixth aspect, a distance from the distal end surface of the cap member to the guide member at the side of the first portion may be larger than a distance from a distal end surface of the restriction member to the distal end surface of the cap member.

DETAILED DESCRIPTION OF THE INVENTION

First Embodiment

An endoscopic tissue resection device according to a first embodiment of the present invention will be described by referring to FIGS. 1 to 9. Hereinafter, the endoscopic tissue resection device will be referred to a "tissue resection device".

Figure 1:
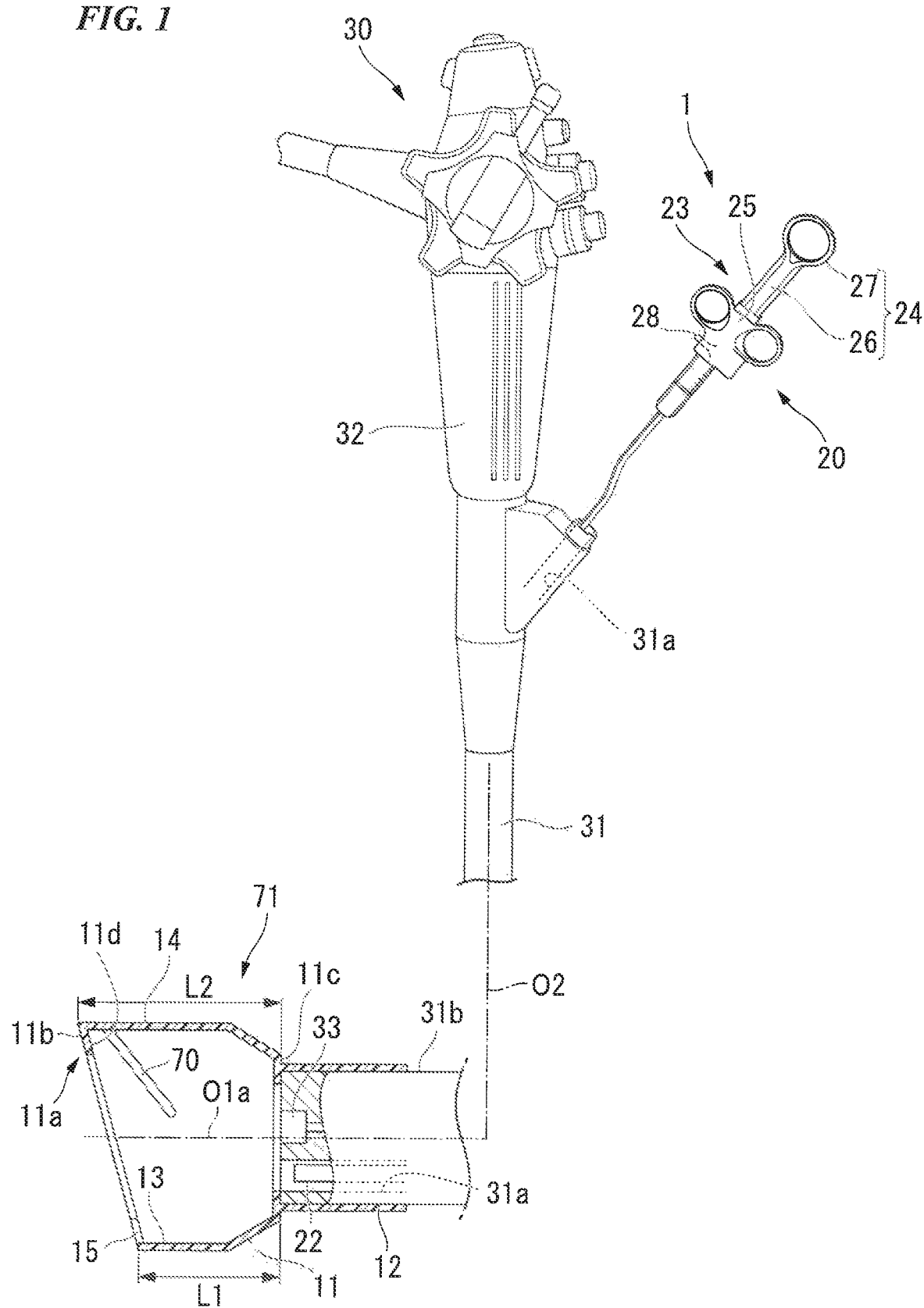
FIG. 1 is a view showing the overall configuration of a medical device according to a first embodiment of the present invention.

FIG. 1 is an overall view showing a state when a tissue resection device 1 according to the present embodiment is attached to an endoscope.

As shown in FIG. 1, the tissue resection device 1 includes a cap member 71 and a high-frequency treatment device 20, and the tissue resection device 1 is a medical device that can be used together with a conventional endoscope 30. For example, the conventional endoscope 30 includes an insertion portion 31 and an operation portion 32. A channel 31a is formed inside the insertion portion 31. The operation portion 32 is disposed for operating a distal end 31b of the insertion portion 31.

The high-frequency treatment device 20 is inserted through the channel 31a to be advanceable and retractable. For example, an internal diameter of the channel 31a is equal to 2.8 millimeters. An imaging portion 33 for observing a treatment target site is disposed at the distal end 31b of the insertion portion 31.

Figure 2:
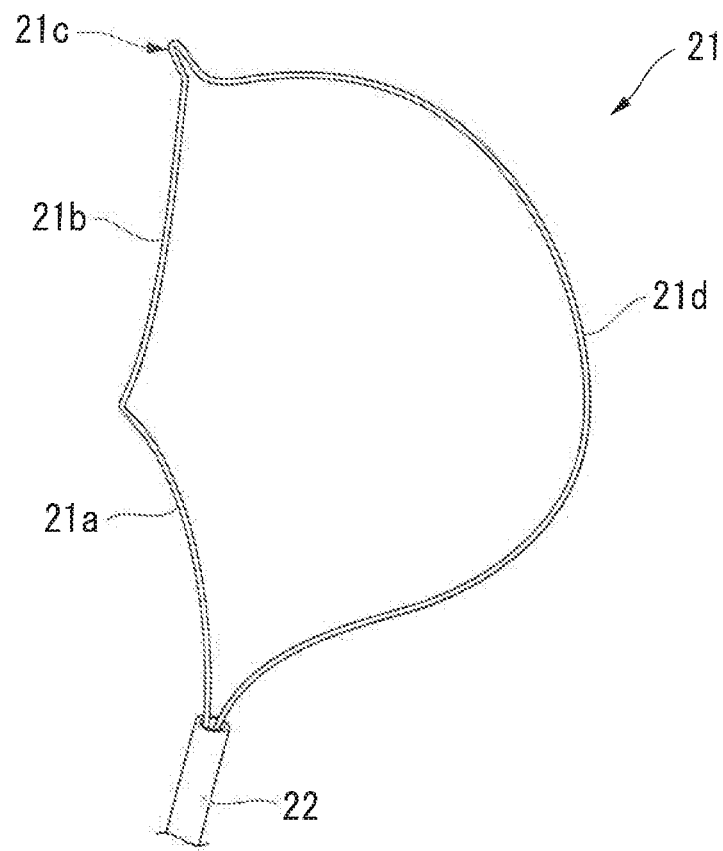
FIG. 2 is a view showing a high-frequency treatment device of the medical device according to the first embodiment of the present invention.

The high-frequency treatment device 20 is a treatment device that can resect the treatment target site. As shown in FIGS. 1 and 2, the high-frequency treatment device 20 includes a snare wire 21, a sheath 22, and a treatment device operation portion 23. The sheath 22 is formed to be able to accommodate the snare wire 21. The treatment device operation portion 23 is disposed at the proximal side of the snare wire 21.

As shown in FIG. 2, the snare wire 21 includes a first wire portion 21a, a second wire portion 21b, a folded portion 21c, and a third wire portion 21d. The snare wire 21 is formed in a substantial loop shape.

The second wire portion 21b extends in a substantial linear shape, while the first wire portion 21a and the third wire portion 21d are formed in bent shapes, respectively. The folded portion 21c is folded to substantial 180 degrees to be in a U-shape.

The snare wire 21 is formed from a conductive material, and the snare wire 21 is energized with a high--frequency current by a high-frequency power supply device (not shown). The snare wire 21 can resect the tissue by contacting the tissue in a high-frequency energized state.

The loop shape of the snare wire 21 described in the present embodiment is only regarded as an example, the snare wire 21 according to the present embodiment may be bent to form a symmetrical loop shape with an axis of the sheath 22 as an axis of symmetry.

As shown in FIG. 2, the sheath 22 is a flexible and substantially tubular member, for example, the sheath 22 is a tube made of resin.

The snare wire 21 is advanceably and retractably inserted through the sheath 22, and the snare wire 21 is configured to be projectable and retractable with respect to a distal end of the sheath 22 in accordance with an operation by the treatment device operation portion 23.

As shown in FIG. 1, the treatment device operation portion 23 includes a main body portion 24 and a slider portion 25. The main body portion 24 is fixed at the proximal side of the sheath 22. The slider portion 25 is attached to the main body portion 24.

The main body portion 24 includes a shaft portion 26 and a finger-hooking ring portion 27. The shaft portion 26 has a center line that is coaxial with respect to the sheath 22. The finger-hooking ring portion 27 is formed at a proximal end of the shaft portion 26. The shaft portion 26 guides the slider portion 25 such that the slider portion 25 moves along the center line of the shaft portion 26.

The slider portion 25 is connected to a proximal end of the snare wire 21. Accordingly, by advancing or retracting the slider portion 25 with respect to the shaft portion 26, the snare wire 21 advances or retracts with respect to the sheath 22. In the present embodiment, when the slider portion 25 is advanced with respect to the shaft portion 26, the snare wire 21 projects from the distal end of the sheath 22. When the slier portion 25 is retracted with respect to the shaft portion 26, the snare wire 21 is retracted to be accommodated inside the sheath 22.

A connector 28 disposed at the slider portion 25 can be connected to the high-frequency power supply device (not shown). The snare wire 21 is electrically connected with the connector 28, and high-frequency current can be supplied to the snare wire 21 via the connector 28.

As shown in FIG. 1, the cap member 71 is attachable to the distal end 31b of the insertion portion 31.

In the present embodiment, the cap member 71 is attached to the distal end 31b of the insertion portion 31 such that a center line (an axis line) O1a of the cap member 71 is almost coincided with a center line O2 of the insertion portion 31.

The cap member 71 is preferably to be transparent in a region overlapping a visual field in order to not to obstruct the visual field. The whole cap member 71 may be formed from a transparent material.

The cap member 71 is substantially tubular having openings at two ends thereof and the cap member 71 defines an internal space. The cap member includes a tubular portion 11, and a connection portion 12. The tubular portion 11 includes a claw portion 11a at the distal end of the tubular portion, the claw portion 11a projecting toward the internal space thereof. The connection portion 12 is provided to be attachable to the distal end 31b of the insertion portion 31.

A distal end surface 11b of the tubular portion 11 contacts with the treatment target site. The distal end surface 11b of the tubular portion 11 is inclined with respect to the center line O1a. An incline angle formed between the distal end surface 11b and the center line O1a is determined based on an approach angle of the endoscope 30 with respect to the treatment target site.

Since the distal end surface 11b is inclined, the tubular potion 11 includes a short shaft portion (a first portion) 13 and a long shaft portion (a second portion) 14. At a side of the short shaft portion 13, a length from the distal end surface 11b to a proximal end surface 11c is defined as L1. At a side of the long shaft portion 14, a length from the distal end surface 11b to the proximal end surface 11c is defined as L2. The tubular portion 11 is configured in a shape that the length L1 at the side of the short shaft portion 13 is shorter than the length L2 at the side of the long shaft portion.

Figure 3:
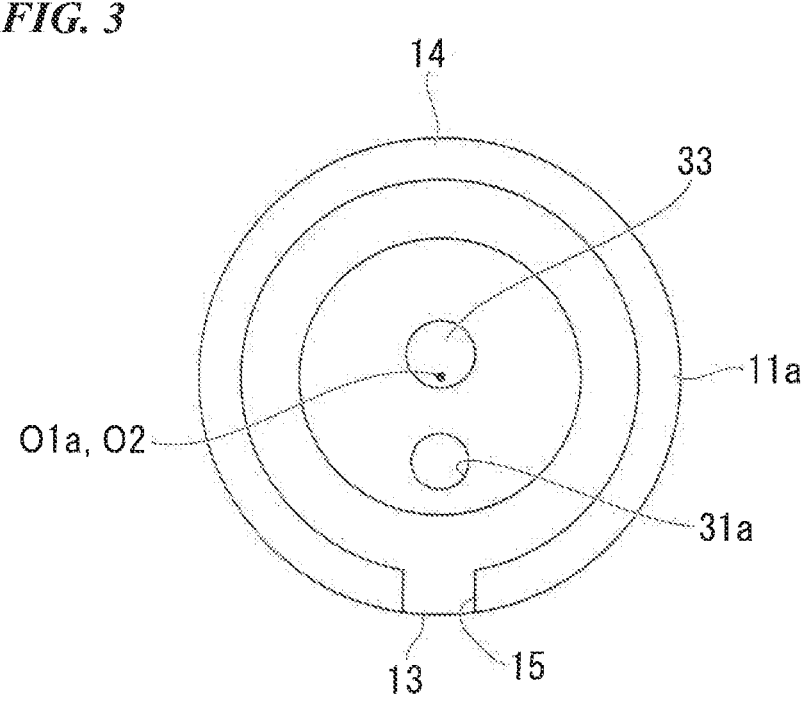
FIG. 3 is a front view showing a cap member of the medical device according to the first embodiment of the present invention.

In the present embodiment, as shown in FIG. 3, the cap member 71 is attached to the distal end 31b of the insertion portion 31 such that the short shaft portion 13 is in phase with the channel 31a, viewed from a direction of the center line O1a or O2. In other words, the cap member 71 is attached to the distal end 31b of the insertion portion 31 such that a position of the channel 31a and a position of the short shaft portion 13 in a circumferential direction of the cap member 71 coincide with each other. In the present embodiment, since a notch portion 15 is formed at a position corresponding to the short shaft portion 13 of the claw portion 11a, the position of the notch portion 15 and the position of the channel 31a in the circumferential direction coincide with each other.

In FIG. 3, in order to simply the description, the configuration without a guide member which is described below is shown.

As shown in FIGS. 1 and 3, the claw portion 11a projects from an internal circumference of the distal end of the tubular portion 11 toward the center line O1a, and the claw portion 11a is formed in a substantial annular shape. An internal surface 11d of the claw portion 11 can be engaged with the snare wire 21. The claw portion 11 is configured to define an opening shape of the distal end portion of the cap member 71 and a dimension thereof, when the cap member 71 is attached to the distal end 31b of the insertion portion 31.

Figure 4:
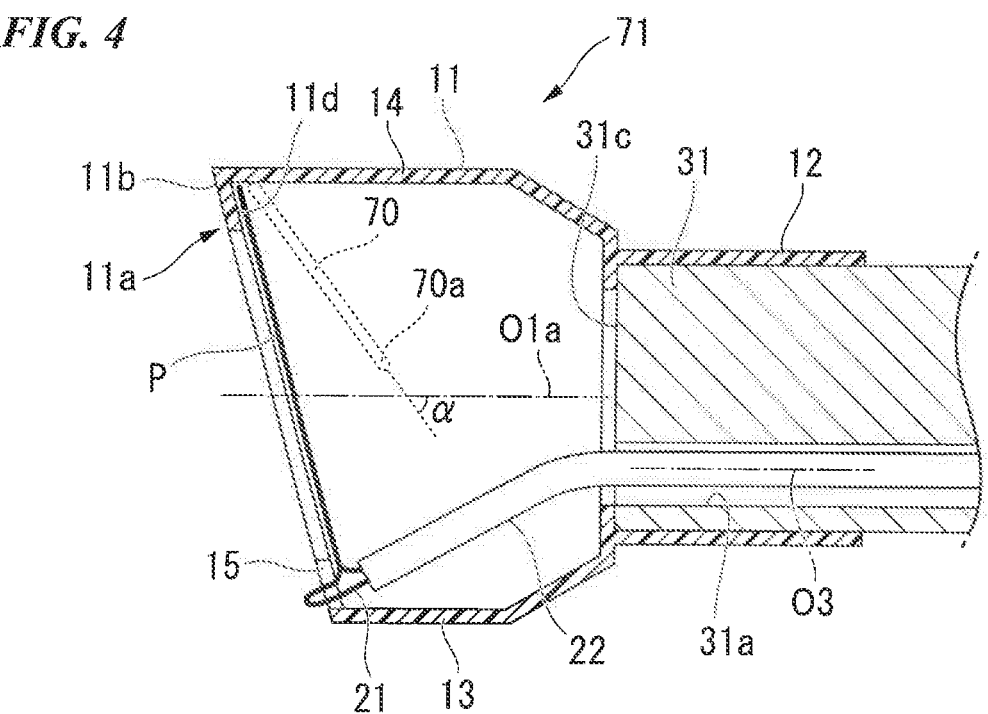
FIG. 4 is a sectional view showing the cap member of the medical device according to the first embodiment of the present invention.

As shown in FIG. 4, a guide member 70 is disposed on an internal surface of the distal end side of the long shaft portion 14 of the cap member 71. The guide member 70 is configured to guide the snare wire 21 along an internal surface thereof such that the snare wire 21 forms a pre-loop P, and the guide member 70 is configured to restrict a retraction of the snare wire toward the side of the insertion portion 31. The pre-loop P is a loop formed by the snare wire 21 which can be suitably used for the desired procedures and can be suitably accommodated in the internal space of the cap member 71.

Both of end port ions 70a of the guide member 70 are extending from the long shaft portion 14 toward the short shaft portion In a lateral view of the cap member 71, the guide member 70 is configured to intersect with the center line O1a of the cap member 71. In the lateral view of the cap member 71, an angle a between the extending direction of the guide member 70 and the center line O1a of the cap member 71 is an acute angle at the proximal end side of the cap member 71. As shown in FIG. 4, in the lateral view of the cap member 71, the angle α formed between the extending direction of the guide member 70 and the center line (axis line) O1a of the cap member 71 is different from an angle (not shown) formed between the annular distal end surface 11b and the center line O1a of the cap member 71.

A region where the guide member 70 is disposed is approximately a half of the internal circumferential surface of the cap member 71.

Next, effects of the tissue resection device 1 according to the present embodiment will be described.

Hereinafter, an example of EMRC by combining the endoscope 30 and the tissue resection device 1 will be described.

Firstly, a return electrode plate (not shown) which is connected to the high-frequency power supply device is attached to a body of a patient as the opposite pole of the snare wire 21 of the high-frequency treatment device 20.

Subsequently, as shown in FIG. 1, the cap member 71 is attached to the distal end 31b of the insertion portion 31 of the endoscope 30. Although it is not shown, a surgeon performs known procedures to insert the endoscope 30 into the body cavity, then guide the distal end of the endoscope 30 to the target treatment site T, and capture the target treatment site T in the visual field of the imaging portion 33.

Figure 5:
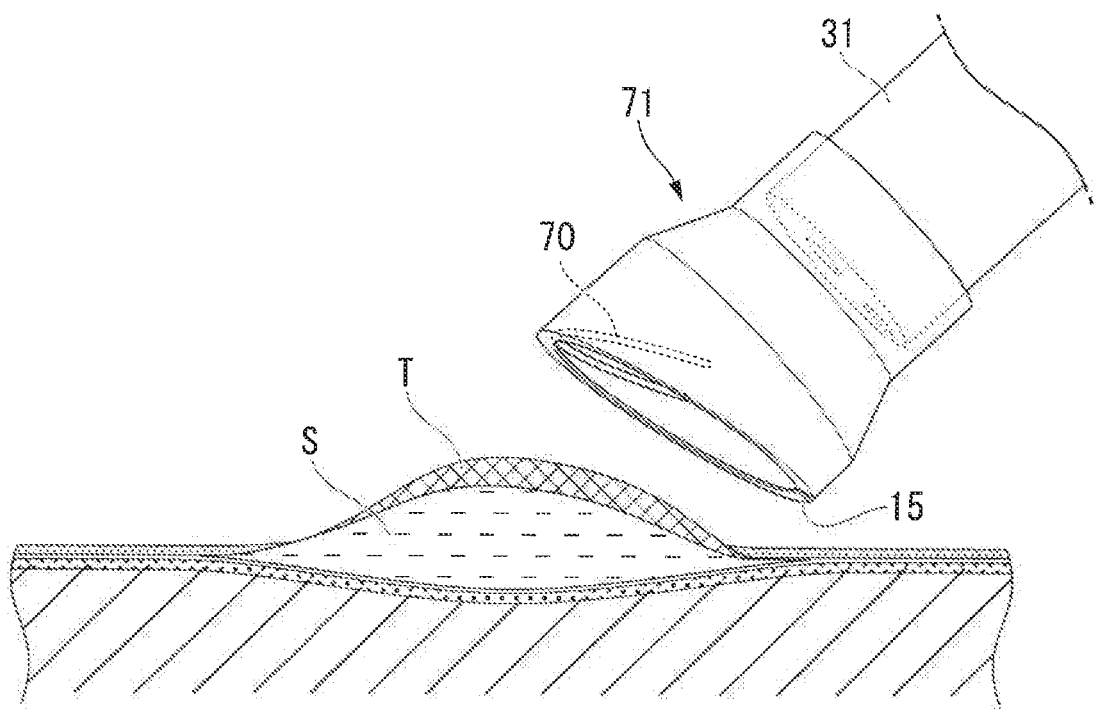
FIG. 5 is a schematic view showing a form of the medical device being used according to the first embodiment of the present invention.

The surgeon uses a local injection needle (not shown) to focally inject the physiological saline S or the like into the submucosal layer of the target treatment tissue T for causing the vicinity of the target treatment tissue T to protrude, as shown in FIG. 5.

Figure 6:
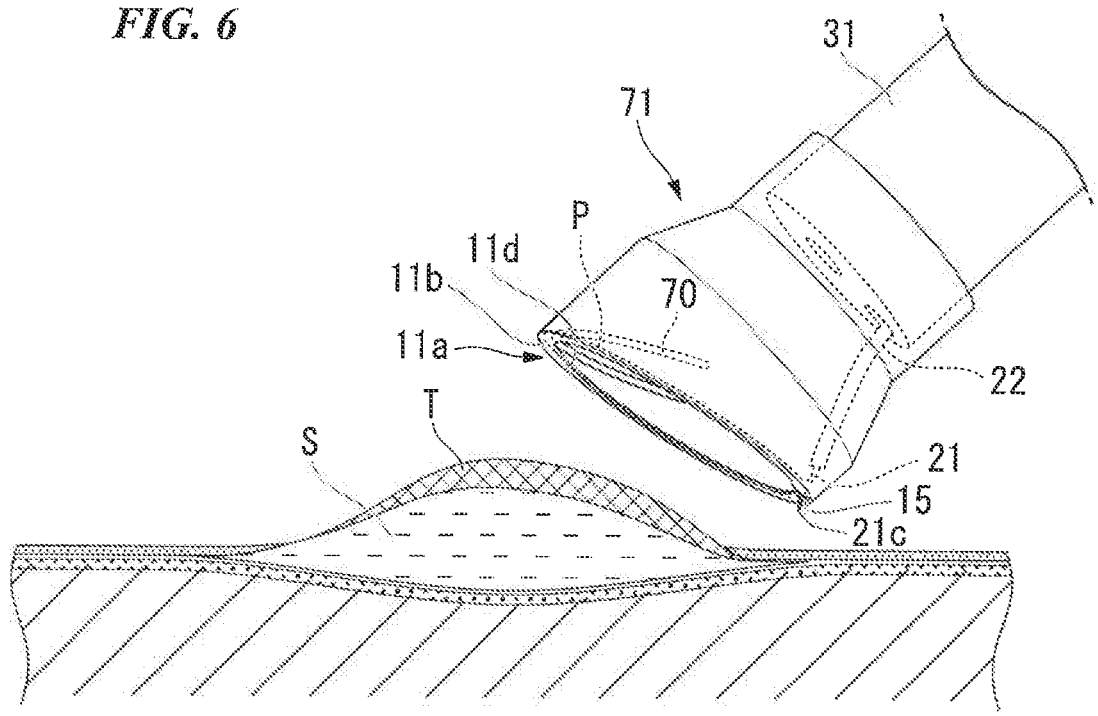
FIG. 6 is a schematic view showing another form of the medical device being used according to the first embodiment of the present invention.

The surgeon inserts the high-frequency treatment device 20 shown in FIG. 1 into the channel 31a of the endoscope 31. The sheath 22 projecting from the distal end of the channel 31a is at a position visually confirmable by using an endoscopic image. As shown in FIG. 1, the surgeon advances and rotates the treatment device operation portion 23 to direct the folded portion 21c of the snare wire 21 toward the notch portion 15. As shown in FIG. 6, in a state when the folded portion 21c is engaged with the notch portion 15, the surgeon slides the slider portion 25 of the treatment device operation portion 23 distally with respect to the shaft portion 26. As a result, the first wire portion 21a, the second wire portion 21b, and the third wire portion 21d which are shown in FIG. 2 are engaged with the internal surface lid of the claw portion 11. At this time, the snare wire 21 is guided along the internal surface 11d of the claw portion 11a to form the pre-loop P by the guide member 70, while the retraction of the snare wire 21 toward the side of the insertion portion 31 is restricted by the guide member 70. Accordingly, the snare wire 21 at the side of die long shaft portion 14 is kept between the internal surface lid of the claw portion 11a and the guide member 70.

As a result, the snare wire 21 with a loop shape (the pre-loop P) is suitably formed inside the tubular portion 11.

Figure 7:
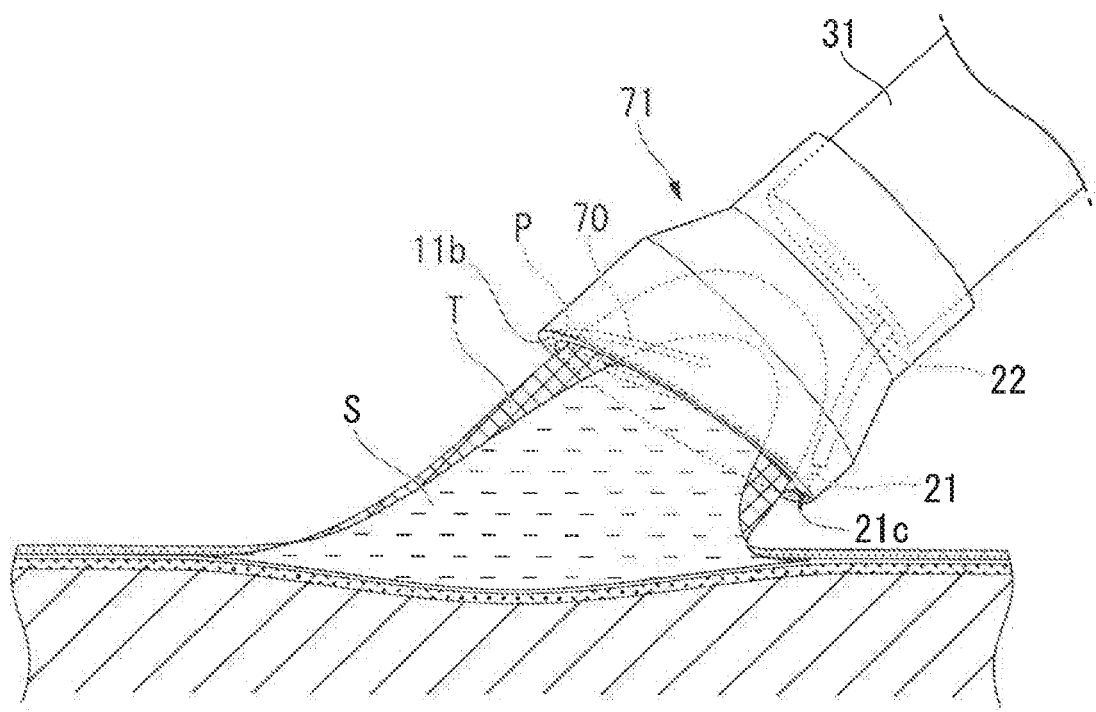
FIG. 7 is a schematic view showing another form of the medical device being used according to the first embodiment of the present invention.

As shown in FIG. 7, the surgeon engages the distal end surface 11b of the cap member 71 with the target treatment site T, and the surgeon uses a suction means (not shown) which is disposed in the endoscope 30 to apply a negative pressure to the space inside the cap member 71. As a result, the surgeon can retract the target treatment site T inside the cap member 71. Inside the cap member 71, since the target treatment site T is retracted from the opening of the cap member 71 to the inside thereof, the target treatment site T comes into the pre-loop P.

In a state when the target treatment site T is retracted into the inside of the cap member 71, the surgeon proximally slides the slider portion 25 of the treatment device operation portion 23 shown in FIG. 1 with respect to the shaft portion 26. Accordingly, the proximal side of the pre-loop P is retracted into the sheath 22, and the target treatment site T is bound.

Subsequently, the surgeon operates the high-frequency power supply device to supply high-frequency current to the high-frequency treatment device 20. The pre-loop P is energized by the high-frequency current, and the target treatment site T bound by the pre-loop P is cauterized and resected.

According to the tissue resection device 1 according to the present embodiment, since the retraction of the snare wire 21 toward the side of the insertion portion 31 is restricted by the guide member 70, it can be prevented that the snare wire 21 at the side of the long shaft portion 14 floats (retracts) toward the side of the insertion portion 31.

Figure 8:
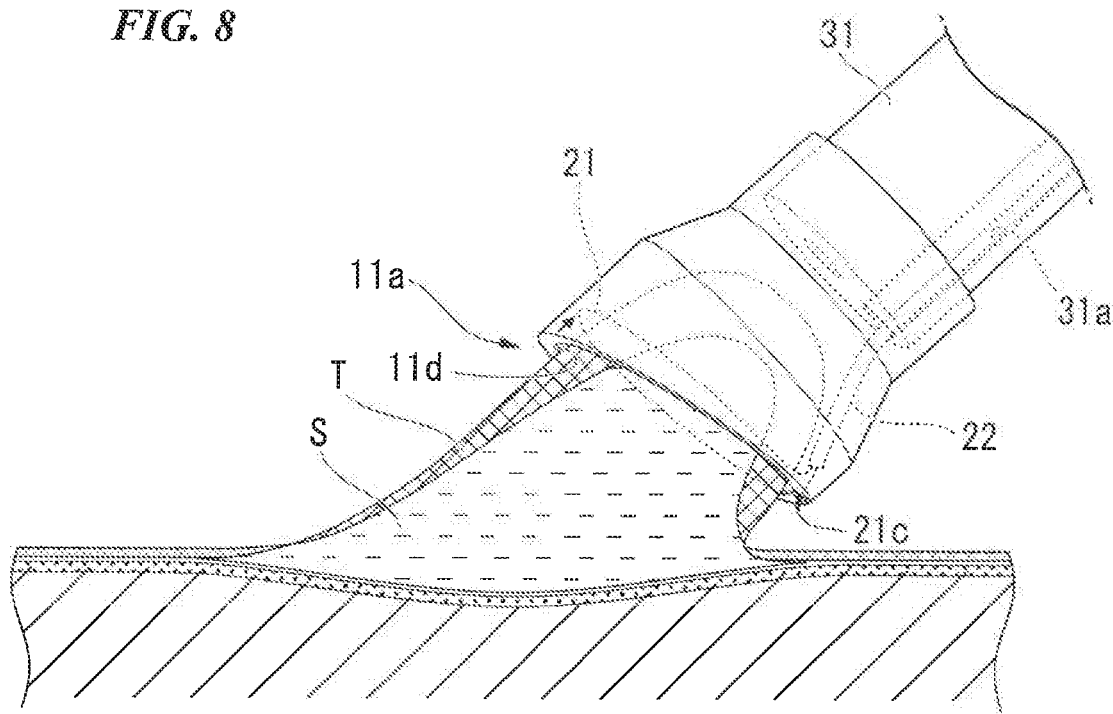
FIG. 8 is a schematic view showing a form of a conventional medical device being used.

As shown in FIG. 8, a conventional cap member is not provided with a guide member. In a situation in which the conventional cap member is used, when the surgeon retracts the target treatment site T into the cap member 71, the folded portion 21c of the snare wire 21 is pressed by the target treatment site T. When the folded portion 21c is pressed, it is possible that the snare wire 21 at the side of the long shaft portion 14 floats (retracts) from the internal surface 11d of the claw portion 11a toward the side of the insertion portion 31. Accordingly, it is possible that the shape of the pre-loop P collapses. However, according to the tissue resection device 1 according to the present embodiment, since the retraction of the snare wire 21 toward the side of the insertion portion 31 is restricted by the guide member 70, the collapse of the pre-loop P can be prevented.

According to the present embodiment, the two ends 70a of the guide member 70 are formed to extend from the long shaft portion 14 toward the short shaft portion 13. In the lateral view of the cap member 71, since the extending direction of the guide member 70 and the axis line of the cap member 71 are intersected with each other to form the acute angle at the proximal end side of the cap member, it is easy to guide the snare wire 21 toward the distal end of the cap member 71.

According to the present embodiment, it is described that the two end portions 70a of the guide member 70 are formed to extend from the long shaft portion 14 toward the short shaft portion 13, it may be configured such that only one end portion 70a of the guide member 70 is formed to extend toward the short shaft portion 13.

According to the present embodiment, it is described that the region where the guide member 70 is disposed is approximately a half of the internal circumferential surface of the cap member 71, the configuration is not limited thereto. The region where the guide member 70 is disposed is not necessary to be the whole circumference, and the above-described effects can be achieved when the region is in a range from a quarter to a half of the whole circumference of the internal surface of the cap member 71 including the side of the long shaft portion 14.

Figure 9:
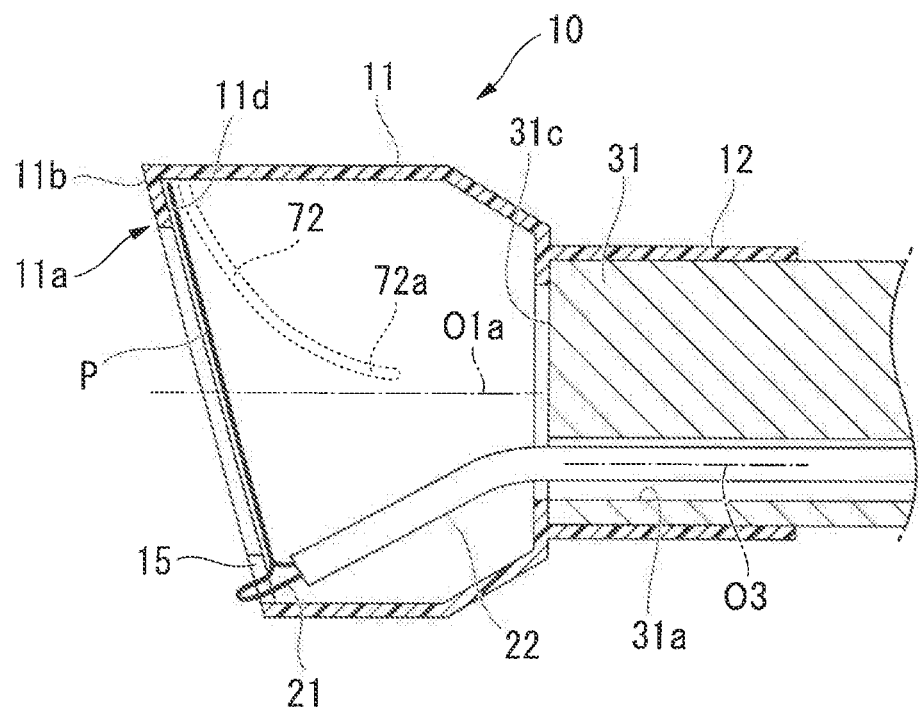
FIG. 9 is a view showing another form of a guide member of the medical device according to the first embodiment of the present invention.

The cap member 70 may not have a linear shape in the lateral view, and as shown in FIG. 9, the end portion 72a of the cap member 72 may be bent toward the connection portion 12.

First Modification

A first modification of the tissue resection device according to the present invention will be described by referring to FIGS. 10 and 11.

The tissue resection device according to the first modification includes a cap member 80 instead of the cap member 71 according to the first embodiment.

In the description of the following variable modifications it is to be noted that like reference numerals designate identical or corresponding components throughout the drawings and duplicate descriptions are omitted.

Figure 10:
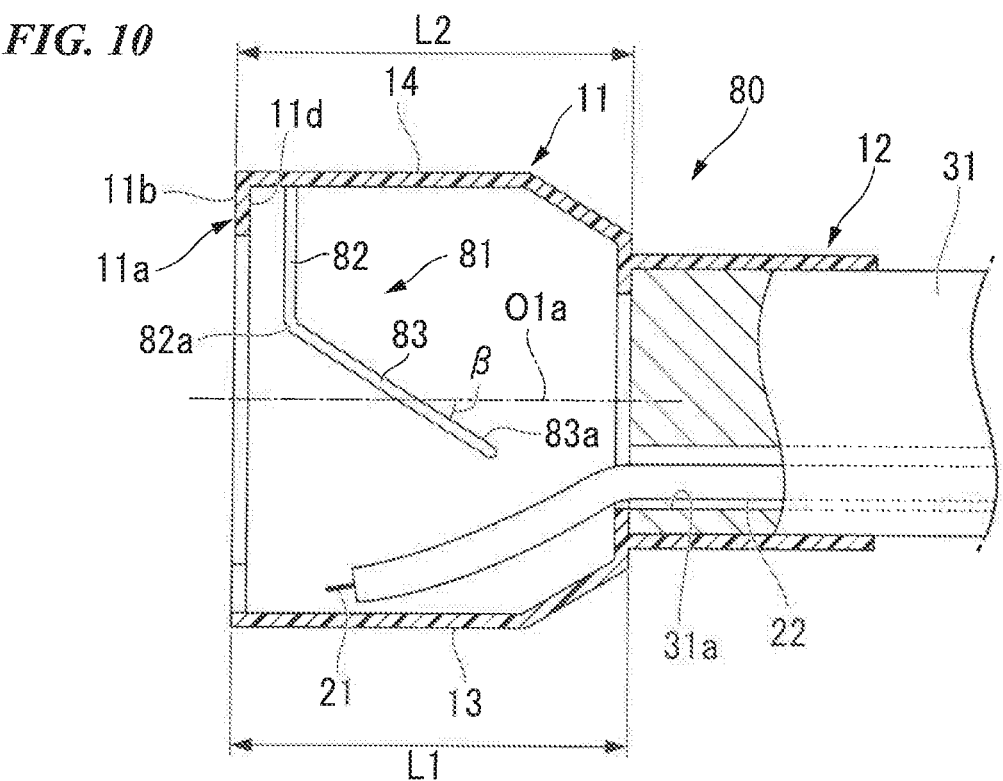
FIG. 10 is a view showing a cap member of a medical device according to a first modification of the present invention.

As shown in FIG. 10, in the cap member 80, the distal end surface 11b of the tubular portion 11 is vertical to the center line O1a. That is, the length L1 of the first portion 13 and the length L2 of the second portion 14 are the same.

Figure 11:
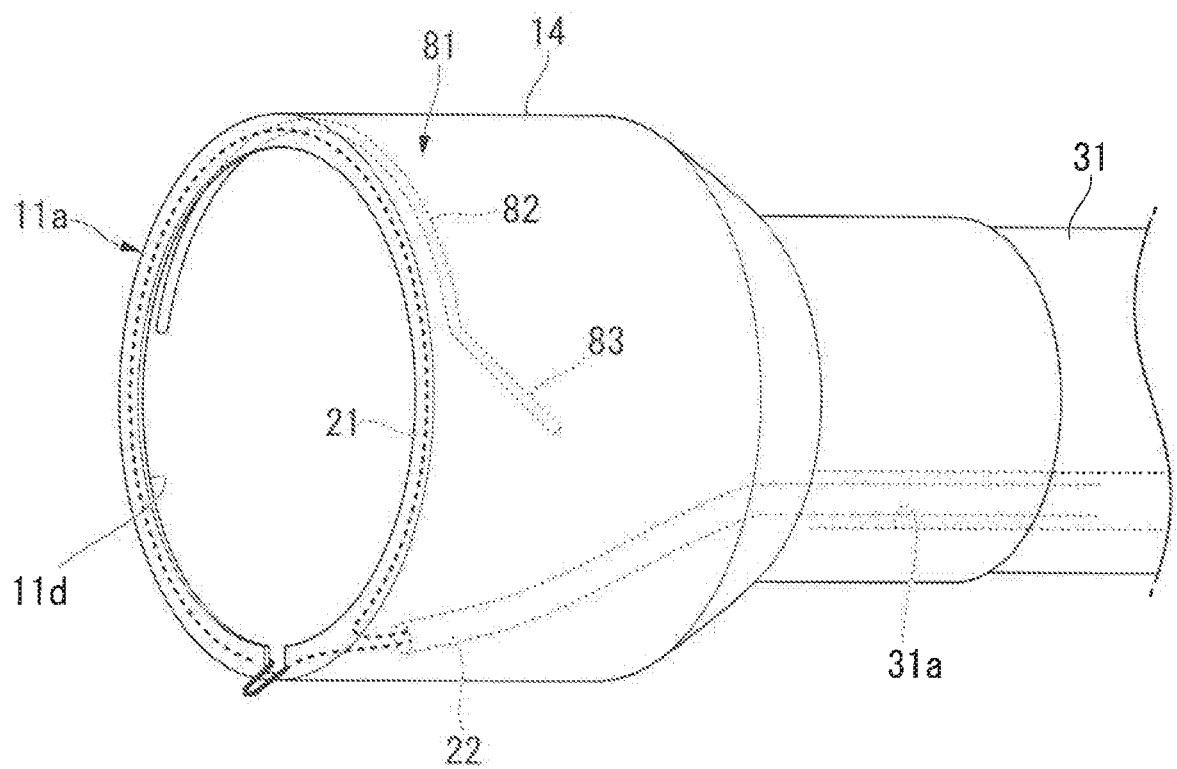
FIG. 11 is a view showing the cap member of the medical device according to the first modification of the present invention.

As shown in FIGS. 10 and 11, a guide member 81 includes a parallel portion 82 and an inclined portion 83. The parallel portion 82 is formed to be parallel to the distal end surface 11b, and the parallel portion 82 is formed at the side of the second portion 14 to be extending toward the side of the first portion 13. The inclined portion 83 is formed to be inclined from an end portion 82a of one side parallel portion 82 toward the side of the first portion 13. In a lateral view of the cap member 80, the inclined portion 83 is disposed to be intersected with the center line O1a. In the lateral view of the cap member 80, an angle β between the extending direction of the inclined portion 83 and the center line O1a of the cap member 80 is an acute angle at the proximal end side of the cap member 80.

According to the first modification, as shown in FIG. 11, when the snare wire 21 projects from the distal end of the sheath 22, the retraction of the snare wire 21 toward the side of the insertion portion 31 is restricted by the guide member 81. Accordingly, the snare wire 21 at the side of the second portion 14 is kept between the internal surface lid of the claw portion 11a and the guide member 81.

According to the first modification, in the cap member 80, the distal end surface 11b of the tubular member 11 is vertical to the center line O1a, in a situation of using this cap member 80, since the parallel portion 82 which is parallel to the distal end surface 11b is disposed at the side of the second portion 14, the retraction of a part of the snare wire 21 that extends from the side of the second portion 14 toward the side of the first portion 13 also can be restricted.

Similar to the first embodiment, the parallel portion 82 can be provided in the cap member 80 in which the distal end surface 11b of the tubular portion 11 is inclined with the center line O1a.

Second Embodiment

A second embodiment of the present invention will be described by referring to FIGS. 12 to 14.

A tissue resection device according to the present embodiment includes a cap member 10 instead of the cap member 71 according to the first embodiment. The cap member 10 is configured to further include a tube body 16 which is different from that of the first embodiment.

In the following description, it is to be noted that like reference numerals designate identical or corresponding components throughout the drawings and duplicate descriptions are omitted.

Figure 12:
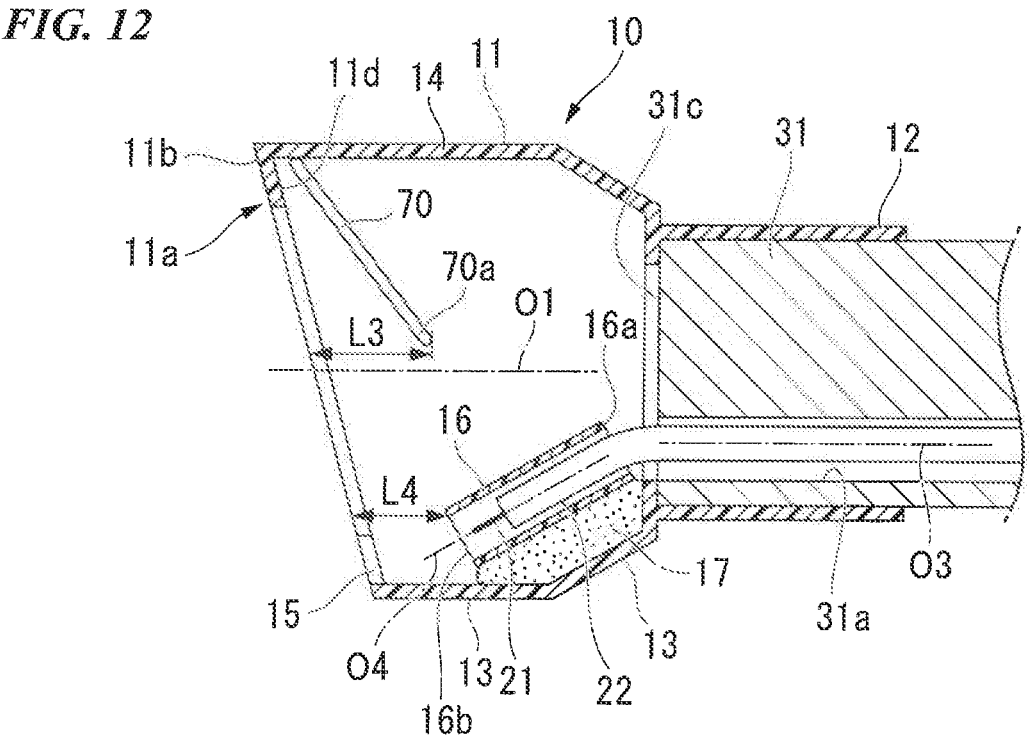
FIG. 12 is a view showing a cap member of a medical device according to a second embodiment of the present invention.

As shown in FIG. 12, the tube body (a restriction member) 16 having a substantially tubular shape is disposed in an internal space of the cap member 10, wherein the internal space in which the tube body 16 is disposed and the center line O1 of the cap member 10 are at opposite sides of a longitudinal axis O3 of the channel 31a. That is, the tube body 16 is disposed in the internal space of the cap member 10 at the side of the short shaft portion 13 of the tubular portion 11. The tube body 16 is configured to define projecting directions of the sheath 22 and the snare wire 21 from the channel 31a. The tube body 16 is configured to restrict a movement of the snare wire 21 in each direction intersecting with the longitudinal axis O3 of the channel 31a (including a horizontal direction).

The tube body 16 is disposed in the internal space of the tubular portion 11 such that a center axis O4 of the tube body 16 is inclined to the longitudinal axis O3 of the channel 31a. The tube body 16 is fixed to the internal surface of the tubular portion 11 by an adhesive agent 17. The adhesive agent 17 is preferably a resin having biocompatibility such as a Polypropylene resin, a Polycarbonate resin, and the like.

The tube body 16 is disposed in the internal space of the cap member 10 in a manner that a first end (the end at the side of the insertion portion 31) 16a of the tube body 16 and a distal end surface 31c of the insertion portion 31 are spaced away from each other with a predetermined clearance. Specifically, the first end 15a of the tube body 16 is directed to the distal end of the channel 31a, and the first end 16a is disposed at a position spaced away from the distal end of the channel 31a with a clearance (for example, about 1 millimeter to 2 millimeters).

A second end (the end at the side of the distal end surface 11b of the cap member 10) 16b of the tube body 16 is directed to the notch portion 15, and the second end 16b is disposed at a position spaced away from the notch portion 15 with a clearance (for example, about 2.0 millimeters to 5.0 millimeters)

Since the tube body 16 is inserted through by the sheath 22, an internal diameter of the tube body 16 is slightly larger than an external diameter of the sheath 22. It is not preferable that the internal diameter of the tube body 16 is too much larger than the external diameter of the sheath 22 since the movement of the sheath 22 cannot be suitably restricted. For example, when the external diameter of the sheath is equal to 2.0 millimeters, the internal diameter of the tube body is preferably 2.8 millimeters. In the present second embodiment, the internal diameter of the tube body 16 is constant to be 2.8 millimeters from the distal end to the proximal thereof.

In the direction along the center line O1 of the cap member 10, a length from the distal end surface 11b of the cap member 10 to the end portion 70a of the guide member 70 is defined to L3, and a length from the distal end surface 11b of the cap member 10 to the second end 16b of the tube body 16 is defined to L4. According to the present embodiment, the guide member 70 and the tube body 16 are disposed in the internal space of the tubular portion 11 such that the length L3 is longer than the length L4.

Next, effects of the tissue resection device according to the present embodiment will be described.

Until the procedure of causing the vicinity of the target treatment tissue T to protrude, the procedures are the same as those according to the first embodiment.

Figure 13:
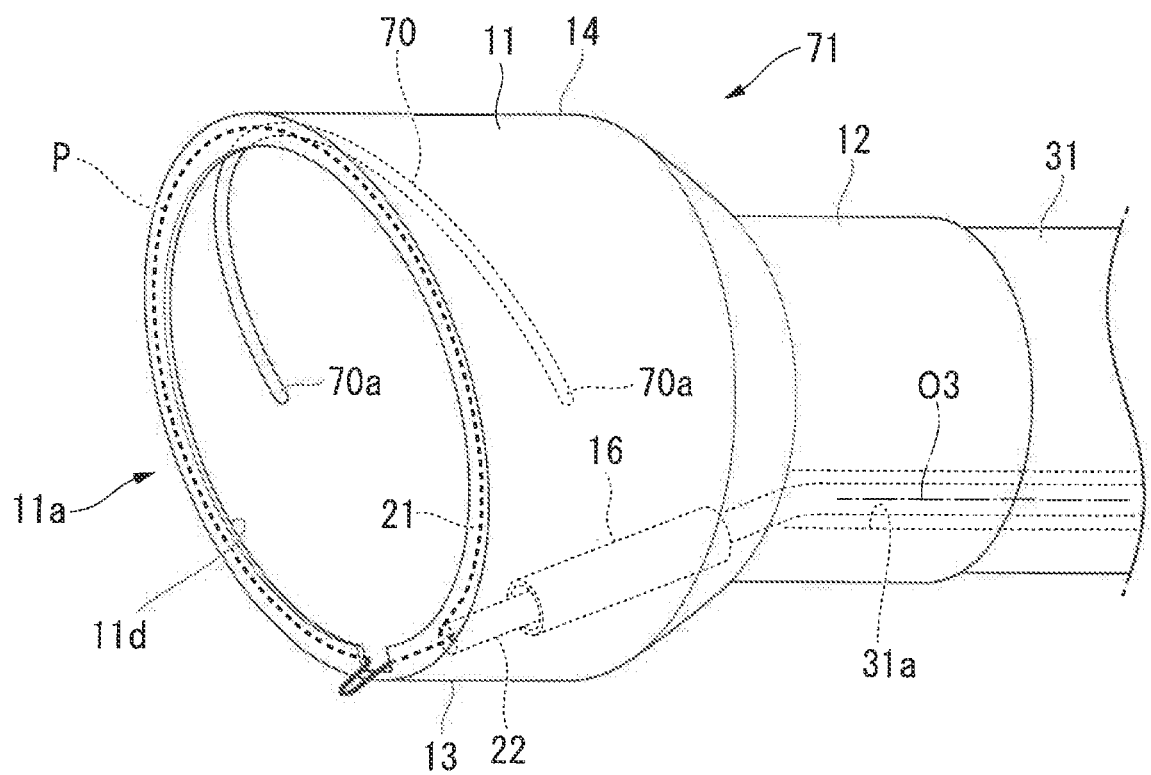
FIG. 13 is a schematic view showing a form of the medical device being used according to the second embodiment of the present invention.

As shown in FIG. 13, the surgeon inserts the sheath 22 through the tube body 16, and projects the distal end of the sheath 22 from the distal end of the tube body 22. The endoscope 30 may be inserted into the body cavity in a state in which the distal end of the sheath 22 is disposed inside the tube body 16.

The surgeon distally slides the slider portion 25 of the treatment device operation portion 23 shown in FIG. 1 with respect to the shaft portion 26. At this time, a displacement of the sheath 22 in the direction intersecting with the center axis O4 of the tube body 16 is suppressed by the tube body 16, and the projecting direction of the snare wire 21 is fixed. In such a state, the first wire portion 21a, the second wire portion 21b, and the third wire portion 21d are engaged with the claw portion 11a along the internal surface lid of the claw portion 11a.

According to the tissue resection device according to the present embodiment, the movement of the sheath 22 in the direction intersecting with the longitudinal axis O3 of the channel 31a is restricted by the tube body 16. Accordingly, the projecting direction of the sheath 22 (snare wire 21) from the channel 31a is defined. As a result, the snare wire 21 definitely projects toward the notch portion 15 and thus it is easy to form the pre-loop P along the internal surface lid of the claw portion 11a.

Figure 14:
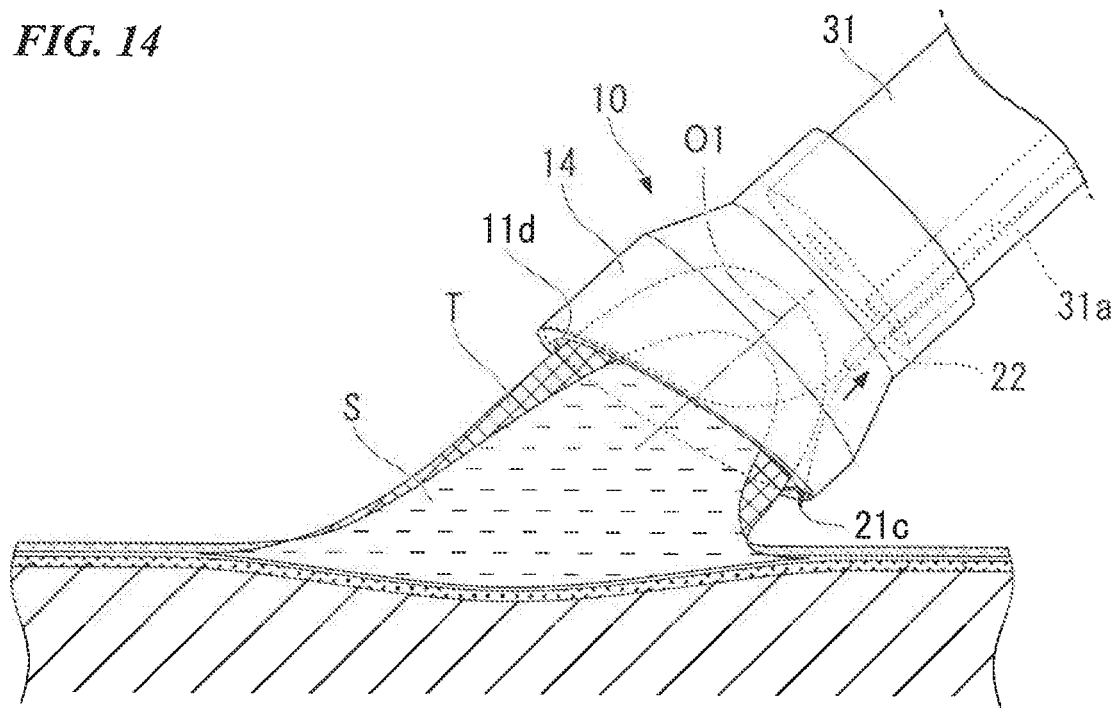
FIG. 14 is a schematic view showing a form of the conventional medical device being used.

On the other hand, as shown in FIG. 14, the tube body (restriction member) is not provided in the conventional cap member. In a situation in which the conventional cap member is used, when the target treatment site T is retracted into the cap member, it is possible that the sheath 22 is pushed back to the side of the insertion portion 31. When the sheath 22 is pushed back, it is possible that the sheath 22 moves to the proximal end side of the channel 31a, or the part of the snare wire 21 at the side of the long shaft portion 14 floats to the side of the insertion portion 31. As a result, there are cases that the shape of the pre-loop P collapses. However, according to the tissue resection device 2 according to the present embodiment, even the sheath 22 retracts, the tube body 16 continues to restrict the projection direction of the snare wire 21 instead of the sheath 22, and thus it is possible to prevent the shape of the pre-loop P from collapsing. Also, as described above, in a situation where the folded portion 21c is pressed, it is possible to prevent the snare wire 21 at the side of the long shaft portion 14 from floating (retracting) from the internal surface 11d of the claw portion 11a to the side of the insertion portion 31. That is, in either of the situation when the sheath 22 is pressed and the situation when the folded portion 21c is pressed, it is possible to prevent the pre-loop P from collapsing.

Further, when the cap member without the tube body (restriction member) is used, there are cases that the sheath 22 projecting from the distal end of the channel 31a directs to the direction of the center line O1 of the cap member 10. In such a situation, it is necessary for the surgeon to advance/retract or rotate the treatment device operation portion 23 that is close at hand to direct the sheath 22 toward the claw portion 11a.

Accordingly, according to the conventional cap member, the procedures become complicated and it is difficult to project the snare wire to be directed to the claw portion 11a.

According to the present embodiment, since the tube body as the restriction member is substantially tubular, it is definitely define the projecting direction of the sheath 22 (snare wire 21).

Since the center axis O4 of the tube body 16 is inclined with the longitudinal axis O3 of the channel 31a, it is easy to protrude the snare wire 21 toward the claw portion 11a.

The tube body 16 is disposed inside the tubular portion 11 in a manner that the first end 16a of the tube body 16 is spaced away from the distal end of the channel 31a. As a result, when the tissue incised by the snare wire 21 is suctioned, the tissue can be suctioned from the space therebetween via the channel 31a.

A second end 16b of the tube body 16 is spaced away from the notch portion 15. When a length from the second end 16b of the tube body 16 to the notch portion 15 is set to be in the above-described range equal to or more than 2.0 millimeters and less than 5.0 millimeters, there are cases that the pre-loop P of the snare wire 21 projecting from the tube body 16 is suitably formed. According to the present embodiment, since the distance between the second end 16b of the tube body 16 and the notch portion 15 is suitably kept, it is easy to form the pre-loop P.

The notch portion 15 is formed at the claw portion 11a and the notch portion 15 is treated as a mark, it is easy to match the channel 31a and the tube body 16 by coinciding the notch portion 15 and the channel 31a in the circumferential direction.

In the cap member 10, since the distal end surface 11b of the tubular portion 11 is inclined with the center line O1, an angle formed between the cap member 10 and the target treatment site T can be small. As a result, it is easy to approach the target treatment site T for the tissue resection device 1.

The position at which the snare wire is projected from the sheath 22 is not limited. According to the present second embodiment, as shown in FIG. 13, the example of projecting the snare wire 21 after the sheath 22 is projected from the distal end of the tube body 16 is described. However, the snare wire 21 may be projected toward the notch portion 15 when the distal end of the sheath 22 is positioned inside the tube body 16. In this case, since the projecting direction of the snare wire 21 can be defined, it is easy to form the pre-loop P.

According to the present embodiment, the example of the cap member 10 in which the distal end surface 11b of the tubular portion 11 is inclined with the center line O1 is described, same effects can be achieved by using a cap member in which the distal end surface 11b of the tubular portion 11 is vertical to the center line O1.

Second Modification

Figure 15:
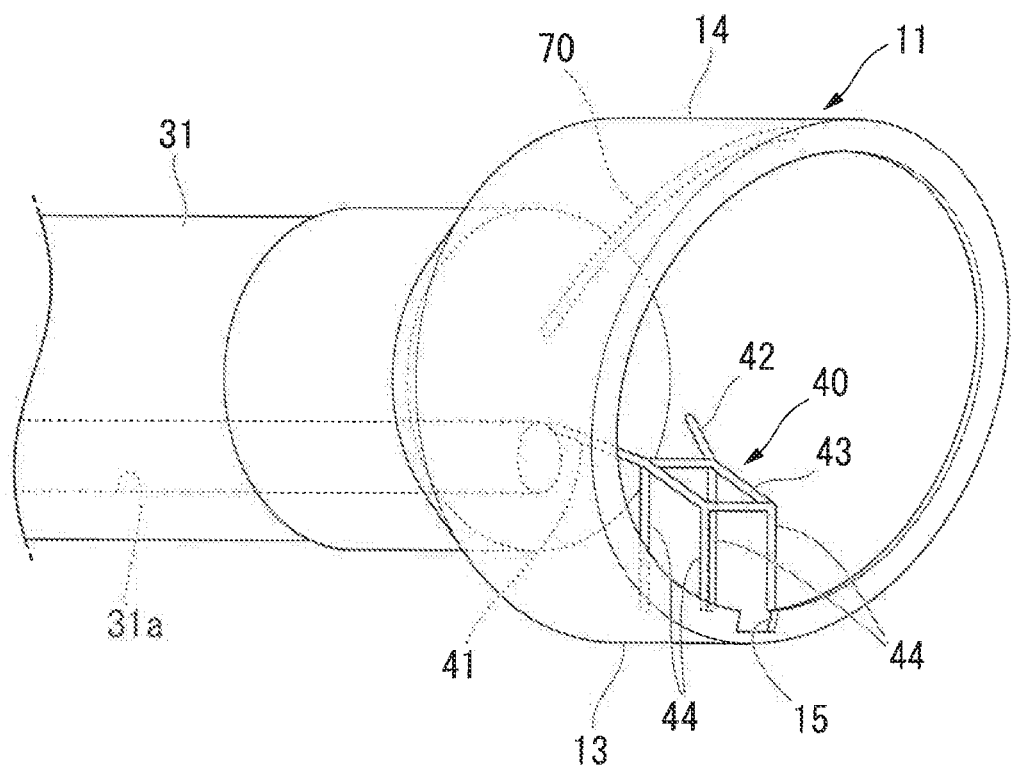
FIG. 15 a view showing a cap member of a medical device according to a second modification of the present invention.
Figure 16:
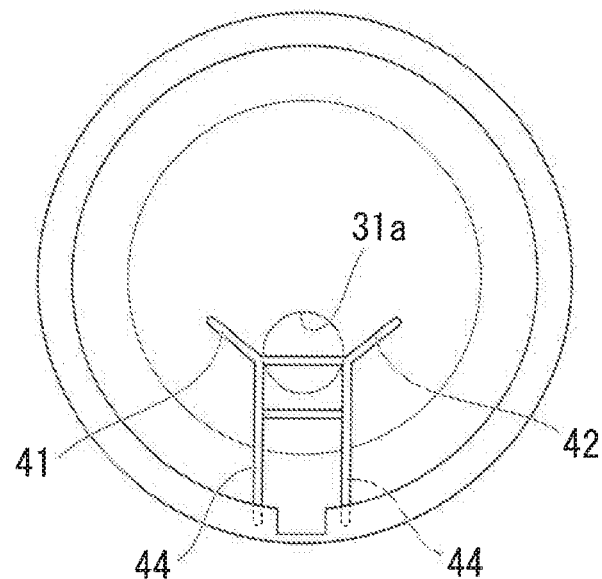
FIG. 16 a view showing the cap member of the medical device according to the second modification of the present invention.

A tissue resection device according to a second modification of the present invention will be described by referring to FIGS. 15 to 17.

The tissue resection device according to the second modification will be described by specifying a configuration of the restriction member different from that of the restriction member according to the second embodiment.

According to the second modification, a wire portion 40 is used as the restriction member. As shown in FIGS. 15 and 16, the wire portion 40 includes a first wire portion 41 and a second wire portion 42, a third wire portion 43, and a leg portion 44. The first wire portion 41 and the second wire portion 42 are disposed to be at the side of the channel 31a. The third wire portion 43 is formed to be a square shape. The leg portion 44 is formed to extend from each vertex of the third wire portion 43 toward the short shaft portion 13. Distal ends of the leg portion 44 are fixed to the internal surface of the tubular portion 11 by the adhesive agent and the like.

A distance between the first wire portion 41 and the second wire portion 42 is gradually increased along a direction toward the insertion portion 31 when viewed from the side of the long shaft portion 14.

Figure 17:
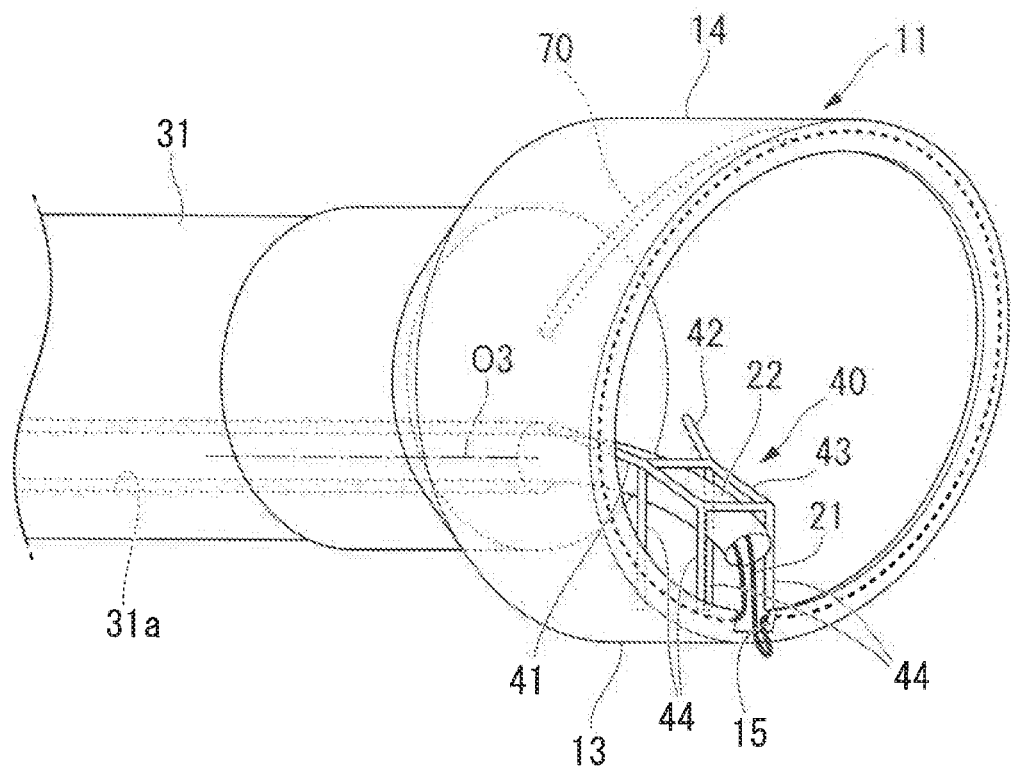
FIG. 17 a view showing the cap member of the medical device according to the second modification of the present invention.

According to the second modification, as shown in FIG. 17, due to the first wire portion 41 and the second wire portion the sheath 22 projected from the channel 31a is easy to enter a space between the leg portions 44 of the proximal end side and the sheath 22 is guided to the space between the leg portion 44 of the distal end side. Since the movement of the sheath 22 is restricted to a direction intersecting with the longitudinal axis O3 of the channel 31a by the wire portion 40, the projecting direction of the sheath 22 from the channel 31a is defined. Further, the retraction of the snare wire 21 toward the side of the insertion portion 31 can be prevented by the guide member 70.

Third Modification

A tissue resection device according to a third modification of the present invention will be described by referring to FIGS. 18 to 20.

The tissue resection device according to the third modification will be described by specifying a configuration of the tube body different from that of the tube body according to the second embodiment.

Figure 18:
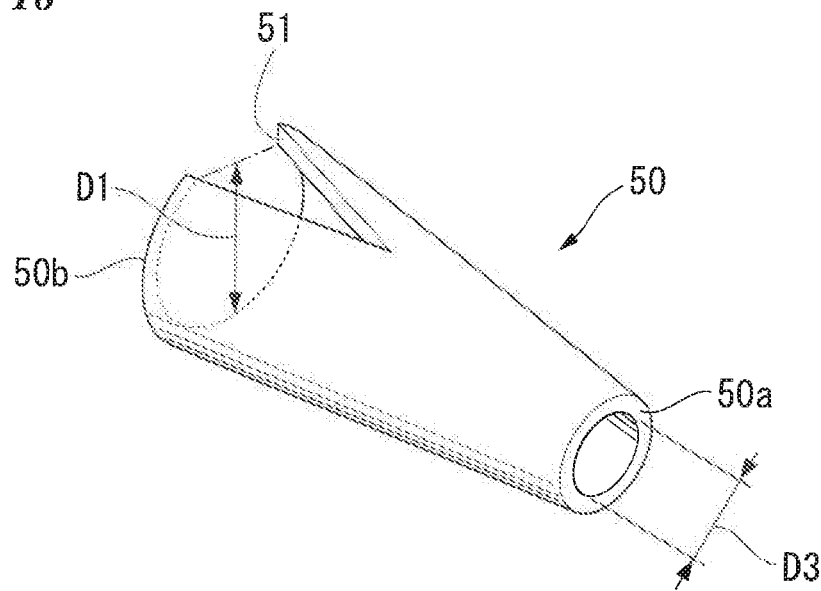
FIG. 18 is a view showing a cap member of a medical device according to a third modification of the present invention.
Figure 19:
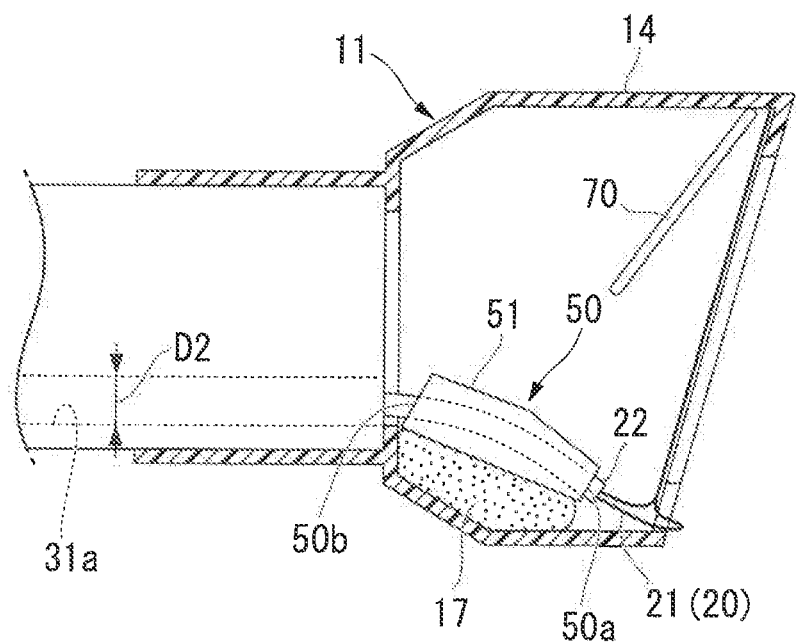
FIG. 19 is a view showing the cap member of the medical device according to the third modification of the present invention.
Figure 20:
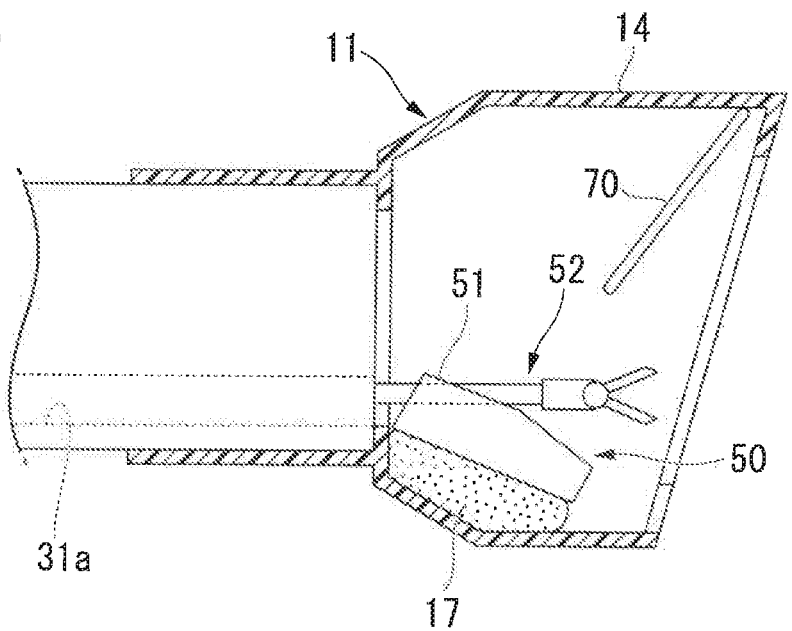
FIG. 20 a view showing the cap member of the medical device according to the third modification of the present invention.

As shown in FIGS. 18 and 19, a tube body 50 is formed in a tapered shape with an internal diameter increasing from a distal end 50a toward a proximal end 50b.

An opening dimension D1 of the proximal end 50b of the tube body 50 is the same with an internal diameter D2 of the channel 31a, an internal diameter D3 of the distal end 50a of the tube body 50 is smaller than the internal diameter D2 of the channel 31a. In the third modification, for example, the opening dimension D1 of the proximal end 50b of the tube body 50 is equal to 2.8 millimeters, and the internal diameter D3 of the distal end 50a of the tube body 50 is equal to 2.1 millimeters. An external diameter of the sheath 22 is 2.0 millimeters.

A notch portion 51 is provided at the proximal end of the tube body 50. As shown in FIG. 19, the notch portion 51 is configured to direct to the side of the long shaft portion 14.

Next, effects of the tissue resection device according to the third modification will be described.

As described above, after the target treatment site T is resected, the surgeon removes the high-frequency treatment device 20 from the endoscope 30, and inserts other treatment devices, for example, such as a grasping forceps 52 into the channel 31a. At this time, as shown in FIG. 20, the surgeon can advance the grasping forceps 52 through the notch portion 51 without inserting the grasping forceps 52 through the inside of the tube body 50. That is, the forceps 52 can project into the internal space of the tubular portion 11 without being disturbed by the tube body 50. Then, the incised target treatment site T is grasped by the grasping forceps 52 and then removed through the channel 31a to the outside of the body.

According to the third modification, since the tube body 50 is formed in a tapered shape, the sheath 22 projected from the channel 31a is easy to enter the tube body 50. The internal diameter D3 of the distal end 50a of the tube body 50 is smaller than the internal diameter D2 of the channel 31a, and thus the internal diameter D3 of the distal end 50a of the tube body 50 is smaller than the opening dimension D1 of the proximal end 50b. Accordingly, the displacement of the sheath 22 can be further suppressed such that the projecting direction of the sheath 22 (the snare wire 21) can be more definitely regulated.

The notch portion 51 is disposed in the tube body 50 such that when the grasping forceps 52 is advanced without passing through the inside of the tube body 50, the grasping forceps 52 can be projected from the channel 31a without being disturbed by the tube body 50.

The notch portion 51 according to the third modification may be formed in the tube body 16 having the constant internal diameter according to the second embodiment.

Fourth Modification

Figure 21:
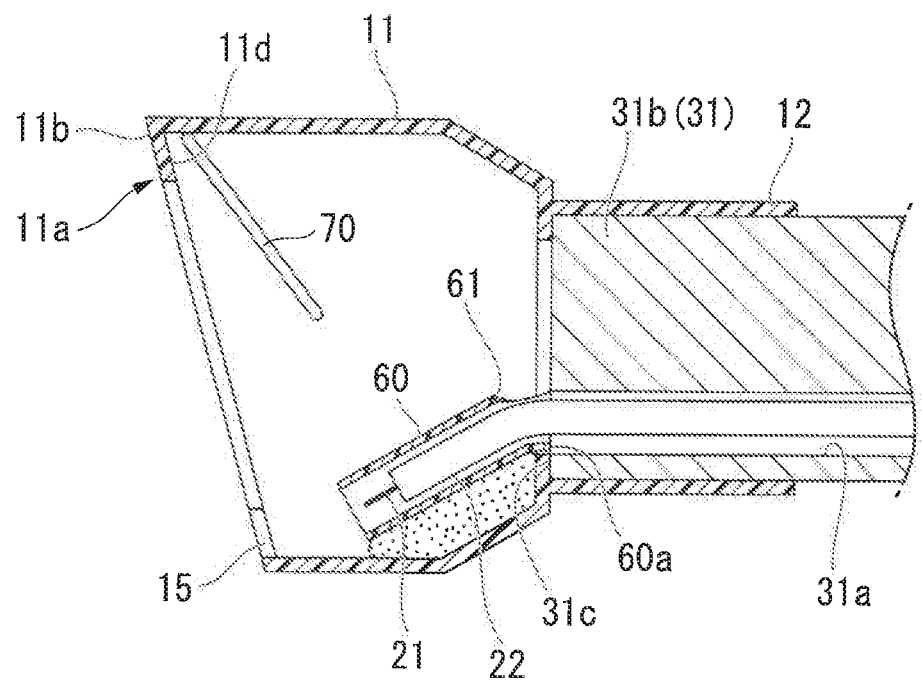
FIG. 21 a view showing a cap member of a medical device according to a fourth modification of the present invention.

A tissue resection device according to a fourth modification of the present invention will be described referring to FIG. 21.

The tissue resection device according to the fourth modification will be described by specifying a configuration and an arrangement of the tube body different from that of the tube body according to the second embodiment.

According to the second embodiment, the tube body 16 is disposed to be spaced away from the distal end of the channel 31a with a clearance, however, according to the fourth modification, the tube body 60 is disposed without any clearance with the distal end of the channel 31a. As shown in FIG. 21, the tube body 60 is disposed in the internal space of the tubular portion 11 such that the first end 60a of the tube body 60 engages with the distal end surface 31c of the insertion portion 31 when the cap member is attached to the distal end 31b of the insertion portion 31.

At the proximal end side of the tube body 60, a communication hole 61 is formed for communicating with the internal space thereof. The communication hole 61 is disposed to face to the side of the long shaft portion 14.

According to the fourth modification, since the tube body 60 is disposed without any clearance with the distal end of the channel 31a, the high-frequency treatment device 20 can be more definitely guided to the tube body 60 when the high-frequency treatment device 20 is inserted through the channel 31a.

Since the communication hole 61 is formed in the tube body 60, when the tissue is incised by the snare wire 21 and suctioned, the tissue can be suctioned via the communication hole 61 and then through the channel 31a.

It is described that the guide member 70 according to the first embodiment can be used as the guide member in the second embodiment and the second modification to the fourth modification, the guide member 72 and the guide member 81 according to the first modification are also applicable.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

For example, the configuration of providing the notch. portion at a part of the claw portion of the cap member is described, the notch portion may not be provided. That is, the claw portion may be formed at the distal end of the cap member with a ring shape.

The configuration of disposing the tube body in a manner that the center axis of the tube body is inclined with the longitudinal axis of the channel is described, the tube body may be disposed in a manner that the center axis of the tube body and the center axis of the channel coincide with each other may be configured in accordance with the shape of the tubular portion.

The guide member may be integrally molded with the tubular portion using the same material of the tubular portion.

[Supplemental Item]

A medical device, including:

a snare wire which is advanceable and retractable inserted through a channel inside an insertion portion of an endoscope, and a cap member which includes a first portion and a second portion and defines an internal space, the first portion being attachable to a distal end of the insertion portion in phase with the channel, wherein a restriction member is configured in the internal space at a side of the first portion of the cap member in order to define a projecting direction of the snare wire projecting from the channel and to restrict a movement of the snare wire toward a horizontal direction intersecting with a longitudinal axis of the channel, wherein a length from a distal end surface to a proximal end surface of the cap member at the side of the first portion is larger than a length from the distal end surface to the proximal end surface of the cap member at a side of the second portion, and wherein a guide member is configured on an internal surface of the distal end side of the cap member at the side of the second portion in order to guide the snare wire to form a loop along the internal surface and to restrict a retraction of the snare wire toward the side of the insertion portion.

What is claimed is:

1. A medical device, comprising:
a snare wire which is advanceably and retractably inserted through a channel formed inside an insertion portion that is inserted through an endoscope;
a substantially tubular cap member which includes a first portion and a second portion that form radially opposite sides of the cap member, the first portion and the second portion being connected to a distal end of the insertion portion, the cap member having an annular distal end surface at a distal end thereof and an internal space formed by the first portion and the second portion, and the first portion being attachable to the distal end of the insertion portion in phase with the channel; and a guide member which is configured to:
   extend along an internal surface of a distal end side of the cap member at a side of the second portion such that: (i) a central axis of the guide member extends in a circumferential direction that is inclined towards the distal end of the cap member at the side of the second portion, and (ii) the guide member continuously extends over a range of a quarter to one half of an entire circumference of the internal surface of the cap member, and
   guide the snare wire to form a loop along the internal surface and to restrict a retraction of the snare wire in a proximal direction toward the insertion portion,
wherein
   in a lateral view of the cap member, the guide member is configured such that an angle formed between an extending direction of the guide member and an axis line of the cap member is different from an angle formed between the annular distal end surface and the axis line of the cap member, and
   the guide member extends from two terminal endsin the circumferential direction that is inclined towards the distal end of the cap member so as to converge at a distal-most portion of the guide member, the two terminal ends being disposed on a proximal side of the distal-most portion and on a side of the first portion relative to the distal-most portion of the guide member.

2. The medical device according to claim 1, wherein:
in the lateral view of the cap member, the extending direction of the guide member and the axis line of the cap member are intersected with each other to form an acute angle at a proximal end side of the cap member.

3. The medical device according to claim 2, wherein a length from the annular distal end surface to a proximal end surface of the cap member at a side of the first portion is shorter than a length from the annular distal end surface to the proximal end surface of the cap member at the side of the second portion.

4. The medical device according to claim 1, wherein the guide member includes a parallel portion which is parallel to the annular distal end surface of the cap member at least at the side of the second portion.

5. The medical device according to claim 1, wherein a region in which the guide member is disposed is smaller than one half of the entire circumference of the internal surface of the cap member.

6. The medical device according to claim 1, further including a restriction member which is disposed in the internal space at a side of the first portion of the cap member so as to define a projecting direction of the snare wire projecting from the channel and to restrict a radially inward movement of the snare wire in a direction intersecting with a longitudinal axis of the channel.

7. The medical device according to claim 6, wherein the restriction member is a tube body through which the snare wire is able to be inserted.

8. The medical device according to claim 7, wherein a center axis of the tube body is inclined with respect to the longitudinal axis of the channel.

9. The medical device according to claim 7, wherein an internal diameter of a distal end of the tube body is smaller than an internal diameter of the channel.

10. The medical device according to claim 6, wherein the restriction member is fixed to the internal surface of the cap member, the internal surface and a center axis of the internal space being on opposite sides with respect to the longitudinal axis of the channel.

11. The medical device according to claim 6, wherein the restriction member is disposed in the internal space of the cap member in a manner that a proximal end of the restriction member is spaced away from the distal end of the insertion portion.

12. The medical device according to claim 6, wherein a communication hole is formed at a proximal end side of the restriction member for communicating with the internal space.

13. The medical device according to claim 6, wherein a notch is formed in a proximal end of a side of the restriction member that faces in a direction toward the second portion.

14. The medical device according to claim 6, wherein a distance from the annular distal end surface of the cap member to the guide member at the side of the first portion is larger than a distance from a distal end surface of the restriction member to the annular distal end surface of the cap member.

15. The medical device according to claim 1, wherein the cap member includes a restriction member that is disposed in the internal space of the cap member at a side of the first portion such that the restriction member is disposed on a radially opposite side of the cap member from the guide member, the restriction member including a passage that extends in a distal direction from a proximal end side of the cap member towards the distal end and is configured to receive the snare wire advanced from the channel in the insertion portion to guide the snare wire from the proximal end side towards the distal end of the cap member.

* * * * *